(12) United States Patent
Urai et al.

(10) Patent No.: US 6,524,559 B2
(45) Date of Patent: Feb. 25, 2003

(54) TOOTH COATING COMPOSITION

(75) Inventors: Kaoruko Urai, Tokyo (JP); Kichizo Tanaka, Tokyo (JP); Kenji Inagaki, Chiba (JP)

(73) Assignee: Hanix Co., Ltd., Tokyo (JP)

( * ) Notice: Subject to any disclaimer, the term of this patent is extended or adjusted under 35 U.S.C. 154(b) by 0 days.

(21) Appl. No.: 10/023,760

(22) Filed: Dec. 21, 2001

(65) Prior Publication Data

US 2002/0119105 A1 Aug. 29, 2002

(30) Foreign Application Priority Data

Dec. 21, 2000 (JP) ........................................ 2000-388248

(51) Int. Cl.⁷ ................................................ A61K 7/16
(52) U.S. Cl. .............................. 424/49; 424/52; 424/58; 424/600; 106/35
(58) Field of Search .............................. 424/49, 52, 58, 424/600; 106/35

(56) References Cited

U.S. PATENT DOCUMENTS 6,048,913 A * 4/2000 Yamagishi et al. ......... 523/118

FOREIGN PATENT DOCUMENTS

| EP | 0900560 A1 * | 3/1999 |
| JP | 07-017822 | 1/1995 |
| JP | 10-203942 | 8/1998 |
| JP | 11-147815 | 6/1999 |

OTHER PUBLICATIONS

Matsumoto et al., Caries Res. 1999, 33(6), 441–445.*

* cited by examiner

Primary Examiner—Marianne C. Seidel
Assistant Examiner—C. Delacroix-Muirheid
(74) Attorney, Agent, or Firm—Browdy and Neimark

(57) ABSTRACT

A tooth coating composition contains shellac, solvent for the shellac, and mica titanium as the main constituents. The coating provided on teeth with such composition is excellent in its drying property, durability, color tone, and easiness of removal thereof. The content of the shellac in the whole composition is preferably from 6 to 12% by weight and the content of the mica titanium is preferably from 3.5 to 16% by weight.

4 Claims, No Drawings

TOOTH COATING COMPOSITION

FIELD OF THE INVENTION

The present invention relates to a tooth coating composition to be applied over teeth for increasing the effects in dental health and/or beautiful appearance.

BACKGROUND OF THE INVENTION

Hitherto, for the purposes of improving the beauty and the health of teeth, various tooth coating compositions have been developed and have been on the market. These tooth coating compositions are required to have the performance such as the safety for the human body, the dispersibility of pigment, the hiding power for covering the blackish portions of teeth, the aesthetic property of the luster of the coat, being hard to cause changes with the passage of time, the easiness of removal of the coat, etc.

Recently, the quality of the products of this kind has been increased, the properties such as the safety, the dispersibility of pigment, the luster, the hiding power, being hard to cause changes with the passage of time, and the easiness of removing the coat are a matter of course, and it is a real situation that the products having the quick drying property capable of finishing coating in a shorter time and the more improved durability in addition to the above-described properties have been more demanded from the consuming public.

Now, as the tooth coating composition, the following techniques are known.

That is, the techniques using a shellac resin as the main constituent, such as the composition comprising an alcohol solution of a shellac resin compounded with a substrate improving agent such as a fish flake paste, etc., a pigment such as titanium oxide, etc.,. and a white turbid preventing agent such as methyl salicylate, etc. (Japanese Patent Laid-Open No. 17822/1995), the composition containing shellac, cellulose ether, a solvent (Japanese Patent Laid-Open No. 203942/1998), the composition comprising an alcohol solution of a shellac resin containing propolis, etc., (Japanese Patent No. 3069540), etc., are the mainstream.

These tooth coating compositions are developed for the purposes of mainly finishing beautifully by covering discolored teeth to put a graze thereon-or preventing the occurrence of the dental caries of teeth, etc., and some of these tooth coating compositions are on the market.

However, the tooth coating composition described in Japanese Patent No. 3069540 has a quick drying property but is very poor in the durability, in the tooth coating composition described in Japanese Patent Laid-Open No. 17822/1995, the hardness and the durability of the coat are improved by compounding a fish flake paste as a substrate-improving agent but on the contrary, the drying property of the coat becomes inferior, and the tooth coating composition described in Japanese Patent Laid-Open No. 203942/1998 has the faults that the composition is lacking in the drying property, and the coat becomes gradually white turbid with the passage of time to deteriorate the appearance.

In the tooth coating composition using shellac as the base, fundamentally, when the content of solid components such as a resin component, etc., is less, a solvent is liable to volatilize and drying of the coat itself is quickened. However, when the content of resin components is less, the coat is thin and the durability thereof is weakened. Thus, it was tried to reduce the content of resin components and compounding a suitable amount of fish flakes or titanium oxide with a tooth coating composition as the durability-strengthening agent of the coat, but although the drying property was very good, the durability could not satisfy the demand.

SUMMARY OF THE INVENTION

Accordingly, an object of the invention is to provide a tooth coating composition having a quick drying property as demanded by general consumers and being excellent in the durability while having the merits of tooth coating compositions of prior art.

As the result of making intensive investigations in view of the above-described circumstances, the present inventors have found that by using specific mica titanium for a tooth coating composition using shellac as the main body, a tooth coating composition, which does not become white turbid for a long time, has a quick drying property, and is excellent in the durability, is obtained and have accomplished the present invention.

DETAILED DESCRIPTION OF THE INVENTION

Then, the present invention described below in detail.

Shellac used in the invention is a resin, which has actual results of being used for foods and has a very high safety. In the tooth coating composition of the invention, the shellac is used as a coat-forming component. The content of such a shellac in the total composition is preferably in the range of from 1% by weight to 20% by weight. When the content of shellac is less than 1% by weight, the coat is too brittle and thus the composition cannot be used as a tooth coating composition. Also, when the content thereof exceeds 20% by weight, the viscosity of the coating liquid is increased, whereby it becomes difficult to thinly coat the composition on teeth and also the drying property becomes inferior. The particularly preferred content of shellac is from 5% by weight to 15% by weight.

In addition to shellac as the coat-forming component, one kind or a combination of two or more kinds of other resins, high molecular materials, and dental cements can be added to the composition at a suitable amount. By adding such material(s), the preferred effects of more improving the luster of the coat and more improving the dispersion of mica titanium or pigments can be expected.

Examples of such a resin include an acrylic resin, a vinyl acetate resin, an alkyd resin, a vinyl chloride resin, a silicone resin, a fluorine resin, rosin, etc.

Examples of the high molecular material include vinylon, nylon, polyvinyl alcohol, polyvinyl pyrrolidone, polyvinyl butyral, polybutene, polyethylene, polypropylene, polyisoprene, cellulose ethers, nitrocellulose, ester gum, viscose rayon, polysaccharide, etc.

Furthermore, examples of the dental cements include zinc phosphate cement, carboxylate cement, glass ionomer cement, zinc oxide euginol cement, silicate cement, etc.

Mica titanium is a substance obtained by coating a mica powder with a thin film of titanium oxide, and fundamentally has been frequently used as a pigment but in the invention, by compounding mica titanium as a coat-strengthening agent, the tooth coating composition excellent in the durability after coating is obtained. Also, by controlling the thickness of the titanium oxide film of the mica titanium, it is possible to obtain an interference color such as yellow, red, blue, green, etc., whereby the tooth coating composition giving a good aesthetic appearance is obtained.

The compounding amount of such a mica titanium in the whole composition is preferably from 0.5% by weight to 30% by weight. When the content of mica titanium is less than 0.5% by weight, the strength of the coat is lowered and the desired durability is not obtained. On the other hand, the content thereof exceeds 30% by weight, the dispersibility thereof in the solution becomes inferior, also, not only after coating, the evaporation of the solution is delayed to reduce the drying property, but also after coating, a rough-feeling sense of incongruity occurs in the mouth. Particularly preferred compounding amount of mica titanium is from 2% by weight to 15% by weight of the whole composition.

The mean particle size of mica titanium used in the invention is in the range of preferably from 5 μm to 50 μm, and more preferably from 10 μm to 30 μm. By using the mica titanium having the mean particle size of from 5 μm to 50 μm, a proper hiding power is imparted to the coat and further the using feeling in the mouth is improved.

As the main solvent of the tooth coating composition of the invention, a lower alcohol-base solvent dissolving shellac is used. As the solvent, which is nontoxic to the human body and dissolves well shellac, there are ethanol, n-propanol, isopropanol, n-butanol, isobutanol, etc., and from the points of the dissolving property and the volatile property, ethanol is most preferred. In addition to the main solvent, as an auxiliary solvent, any solvent, which is safe for the human body and gives less stimulation in the mouth, may be used. For example, as an auxiliary solvent, there are water, propylene glycol, glycerol, etc. Propylene glycol and glycerol are also frequently used as the solvents for general cosmetics and are used for dissolving medical components and extracts.

To the tooth coating composition of the invention can be added a chemical having an anti-cariogenic action. As such a chemical having an anti-cariogenic action, there are sodium fluoride, sodium monofluorophosphate, stannous fluoride, and polyphenol-containing vegetable extract.

There are actual results that sodium fluoride, sodium monofluorophosphate, or stannous fluoride is properly compounded in dentifrices as a medical component having an anti-cariogenic action and many products are on the market. Also, it is known that the polyphenol-containing vegetable extract has an antimicrobial action to the S. Mutans bacteria, which is a decayed tooth bacteria, and the extract is considered to be a very effective dental carries preventing agent.

Practical examples of the polyphenol-containing vegetable extract include one or more extracts selected from the group consisting of a fig extract, a hydrangea tea extract, an oolong tea extract, a tea extract, a grape seed extract, a grape rind extract, a blue berry extract, an apple extract, a eucalyptus extract and a rosemary extract.

By compounding the above-described medicine having the anti-cariogenic action with the tooth coating composition of the invention, without making a troublesome action such as teeth polishing such as brushing, etc., the dental caries preventing effect can be expected.

Also, the tooth coating composition of the invention can, if necessary, contain various coloring agent. Examples of such a coloring agent include zinc oxide, titanium oxide, barium sulfate, mica, carbon black, white carbon, calcium hydrogenphosphate, calcium tertiary phosphate, hydroxy apatite, iron oxide, chromium oxide, magnesium oxide, calcium oxide, aluminum oxide, fish flakes, talc, calcium carbonate, magnesium carbonate, barium carbonate, and tar dyes.

Furthermore, the tooth coating composition of the invention can contain, if necessary, various pharmaceutical components other than the above-described substances and also spicery, an antiseptic, a buffer, s pH controlling agent, a surface active agent, a dispersing agent, a plasticizer, a ultraviolet absorbent, a viscosity controlling agent, an antioxidant, etc.

The pharmaceutical components include sodium azulenesulfonate, $\epsilon$-aminocaproic acid, allantoin, allantoin chlorohydroxy aluminum, allantoin dihydroxy aluminum, epidihydrocholestrin, dihydrocholesterol, sodium chloride, glycyrrhizinic acid, diammonium glycyrrhizinate, di-sodium glycyrrhizinate, tri-sodium glycyrrhizinate, di-potassium glycyrrhizinate, mono-ammonium glycyrrhizinate, $\beta$-glycyrrhizinic acid, isopropyl methyl phenol, cetylpyridinium chloride, decalinium chloride, benzalkonium chloride, benzethonium chloride, alkyldiaminoethylglycine hydrochloride, chlorohexidine hydrochloride, tricrosane, ascorbic acid, sodium ascorbate, pyridoxine hydrochloride, dl-$\alpha$-tocopherol acetate, dl-$\alpha$-tocopherol nicotinate, zeolite, di-sodium dihydrogen pyrophosphate, sodium pyrophosphate, sodium hydrogenphosphate, sodium tertiary phosphate, sodium polyphosphate, polyethylene glycol, polyvinyl pyrrolidone, lysozyme chloride, copper chlorophyllin sodium, hinokitiol, polyoxyethylene lauryl ether, lauroylsarcosine sodium, etc.

The above-described pharmaceutical components have the actual results of being compounded with dentifrices and are preferred materials as the materials of being used in the mouth. As the pharmaceutical effects thereof, there are, in addition of the prevention of dental caries, the prevention of halitosis, the prevention of the deposition of tartar, the prevention of gingivalise.gingivitis, the effect of removing nicotine, etc.

In addition, as the dispersing agent described above, there is an N-methacrolylethyl-N,N-dimethylammoniume. $\alpha$-N-methylcarboxybetainee.butyl methacrylate copolymer. The compound functions as a good dispersing agent.

EXAMPLES

Then, the invention is described in more detail by the following examples.

Example 1

By mixing well 18.0% by weight of Lack Coat 50 EDS (50% ethanol solution of shellac, manufactured by Nippon Shellac K.K.), 72.0% by weight of absolute ethanol, and 10.0% by weight of mica titanium (mean particle size: 25 μm) by a stirrer, a desired composition was obtained. The content of the shellac in the whole composition in the example was 9.0% by weight.

Example 2

By mixing well 20.0% by weight of Lack Coat 50 EDS, 67.1% by weight of absolute ethanol, 10.0% by weight of mica titanium (mean particle size: 35 μm), 0.20% by weight of sodium fluoride, 2.5% by weight of titanium oxide and 0.2% by weight of a charcoal dry distillated liquid by a stirrer, a desired composition was obtained.

Example 3

By mixing well 16.0% by weight of Lack Coat 50 EDS, 69.0% by weight of absolute ethanol, 8.5% by weight of mica titanium (mean particle size: 5 μm), 2.5% by weight of a eucalyptus extract, 3.0% by weight of a grape rind extract, and 1.0% by weight of spicery by a stirrer, a desired composition was obtained.

Example 4

By mixed well 24.0% by weight of Lack Coat 50 EDS, 55.7% by weight of absolute ethanol, 13.5% by weight of mica titanium (mean particle size: 50 μm), 0.6% by weight of a charcoal dry distillated liquid, 5.0% by weight of a rosemary extract, and 1.2% by weight of spicery by a stirrer, a desired composition was obtained.

Example 5

By mixing well 18.0% by weight of Lack Coat 50 EDS, 74.0% by weight of absolute ethanol, 3.5% by weight of mica titanium (mean particle size: 10 μm), 3.5% by weight of titanium oxide, and 1.0% by weight of calcium hydrogenphosphate by a stirrer, a desired composition was obtained.

Example 6

By mixing well 12.0% by weight of Lack Coat 50 EDS, 65.18% by weight of absolute ethanol, 16.0% by weight of mica titanium (mean particle size: 5 μm), 1.0% by weight of an acrylic acid polymer (polyacrylic acid), 2.5% by weight of mica, 0.3% by weight of zinc oxide, 3.0% by weight of a grape rind extract, and 0.02% by weight of tricrosane by a stirrer, a desired composition was obtained.

Example 7

By mixing well 20.0% by weight of Lack Coat 50 EDS, 69.19% by weight of absolute ethanol, 0.8% by weight of mica titanium (mean particle size: 25 μm), 8.5% by weight of mica, 0.01% by weight of benzethonium chloride, and 1.5% by weight of spicery by a stirrer, a desired composition was obtained.

Example 8

By mixing well 50.0% by weight of Lack Coat 50 EDS, 44.8% by weight of absolute ethanol, 2.5% by weight of mica titanium (mean particle size: 20 μm), 1.5% by weight of titanium oxide, and 1.2% by weight of spicery by a stirrer, a desired composition was obtained.

Example 9

By mixing well 18.0% by weight of Lack Coat 50 EDS, 76.4% by weight of absolute ethanol, 0.1% by weight of mica titanium (mean particle size: 25 μm), and 5.5% by weight of fish flakes by a stirrer, a desired composition was obtained.

Comparative Example 1

By mixing well 20.0% by weight of Lack Coat 50 EDS, 72.5% by weight of absolute ethanol, 5.0% by weight of fish flakes, and 2.5% by weight of methyl salicylate by a stirrer, a composition for a comparative test was obtained.

Comparative Example 2

By mixing well 10.0% by weight of Lack Coat 50 EDS, 85.3% by weight of absolute ethanol, 3.5% by weight of titanium oxide, and 1.2% by weight of spicery by a stirrer, a composition of a comparative test was obtained.

(Test 1: Durability test) For 20 testees, each coating composition was coated on 8 front teeth of the upper jaw at 9 a.m., and thereafter, they spent an ordinary food life (however, during the term of the test, teeth polishing by brushing was prohibited.).

At 9 p.m. after 12 hours since coating the compositions, the remaining states of the coated films were observed. For testing for minimum 11 days in regard to 11 samples of Examples 1 to 9 and Comparative Examples 1 and 2, there was established no particular restriction on eating and drinking for 20 testees.

The results were evaluated as follows.

No peeling: 3 marks

Only tip peeled: 2 marks

⅓ Peeled: 1 mark

More ⅓ peeled: 0

Per one sample, 20 testees, the sum total marks of total 160 teeth were calculated and from the values, the average mark per one tooth was calculated.

(Test 2: Color tone test)

In the test 1, the color tone of each coat after 12 hours was observed. The results were evaluated as follows.

No white turbidity or no conspicuous: 2 marks

White turbid but not so conspicuous: 1 mark

Clearly white turbid to give incongruity feeling: 0

Per one sample, 20 testees, the sum total marks of total 160 teeth were calculated and from the values, the average mark per one tooth was calculated.

(Test 3: Drying property test)

In the test 1, the speed of drying the coat after coating on the teeth was observed. The results were evaluated as follows.

Dried within 10 seconds: 2 marks

Dried from 10 to 30 seconds: 1 mark

Dried after at least 30 seconds: 0

Per one sample, 20 testees, the sum total marks of total 160 teeth were calculated and from the values, the average mark per one tooth was calculated.

(Test 4: Removing property test)

In the test 1, after 12 hours, polishing by ordinary rushing using a toothbrush was performed (without using tooth powder), the extent of the removal of the coat was observed. The results were evaluated as follows.

Completely removed: 2 marks

About 1/2 remained: 1 mark

More than 1/2 remained: 0

Per one sample, 20 testees, the sum total marks of total 160 teeth were calculated and from the values, the average mark per one tooth was calculated.

About the samples of Examples 1 to 9 and Comparative Examples 1 and 2, the durability test, the color tone test, the drying property test, and the removing property test described above were carried out and the results are shown in Table 1.

TABLE 1

| | Tooth Coating Composition Property Test | | | |
|---|---|---|---|---|
| | Test 1 (Durability) | Test 2 (Color Tone) | Test 3 (Drying Property) | Test 4 (Removing Property) |
| Example 1 | 2.8 | 1.9 | 1.9 | 2.0 |
| Example 2 | 2.8 | 1.8 | 1.8 | 2.0 |
| Example 3 | 2.8 | 1.9 | 1.9 | 2.0 |
| Example 4 | 2.7 | 1.7 | 1.7 | 2.0 |
| Example 5 | 2.6 | 1.9 | 1.9 | 2.0 |
| Example 6 | 2.5 | 1.9 | 1.9 | 2.0 |
| Example 7 | 2.7 | 1.9 | 1.9 | 2.0 |
| Example 8 | 2.0 | 0.4 | 0.2 | 1.8 |

TABLE 1-continued

Tooth Coating Composition Property Test

|  | Test 1 (Durability) | Test 2 (Color Tone) | Test 3 (Drying Property) | Test 4 (Removing Property) |
|---|---|---|---|---|
| Example 9 | 1.7 | 1.8 | 1.8 | 2.0 |
| Comparative Example 1 | 1.9 | 1.7 | 1.8 | 2.0 |
| Comparative Example 2 | 1.4 | 1.6 | 1.8 | 2.0 |

As is clear from the above-described comparative tests:
(1) The whole compositions (Examples 1 to 7) containing from 6.0 to 12.0% by weight of shellac and from 3.5 to 16% by weight of mica titanium satisfy the durability, the color tone, the drying property and the removing property.

(2) When the amount of shellac is increased too much (Example 8: the content of shellac is 25.0% by weight), the drying property becomes extremely inferior and also the color tone is reduced (becomes white turbid), and the durability and the removing property become inferior.

(3) When the amount of mica titanium becomes less (Example 9: 0.1% by weight, Comparative Examples 1 and 2: 0% by weight), the durability becomes inferior.

Effect of the Invention (1) According to the invention of claim 1, by incorporating mica titanium in a resin composition containing shellac as the base, a tooth coating composition, which has a proper drying property and can easily carried out a brush coating work to teeth, as well as has the effects that the coat coated on the teeth is strong and is not peeled off by taking an ordinary meal, the color tone of the coat is natural and has a luster, the coat is not whitened with the passage of time, and in the case of removing the coat, the coat can be easily removed by a tooth brush, etc., can be provided.

(2) According to the invention of claim 2, by incorporating from 1 to 20% by weight of shellac in the invention of claim 1, the durability, the color time, the drying property and the easiness of removing of tooth coating composition can be more improved.

(3) According to the invention of claim 3, by incorporating from 0.5 to 30% by weight of mica titanium in the invention of claim 1, the durability of the tooth coating composition can be improved.

(4) According to the invention of claim 4, by using mica titanium having a mean particle size of from 5 to 50 μm in the invention in one of claim 1, the durability of the tooth coating composition can be more improved.

(5) According to the inventions of claim 3 and claim 4, since a medicine having an anti-cariogenic action is used in the invention of one of claim 1, the tooth coating composition having an anti-cariogenic property can be provided.

What is claimed is:

1. A tooth coating composition comprising 6–12% shellac, a solvent of the shellac, and 3.5–16% mica titanium as the main constituents.

2. The tooth coating composition according to claim 1, wherein the mean particle size of the mica titanium is from 5 μm to 50 μm.

3. The tooth coating composition according to claim 1, wherein the tooth coating composition further contains one or more selected from the group consisting of sodium fluoride, sodium monofluorophosphate, stannous fluoride, and a polyphenol-containing vegetable extract.

4. The tooth coating composition according to claim 3, wherein the polyphenol-containing vegetable extract is one or more extracts selected from the group consisting of a fig extract, a hydrangea tea extract, an oolong tea-extract, a tea extract, a grape seed extract, a grape rind extract, a blue berry extract, an apple extract, a eucalyptus extract and a rosemary extract.

* * * * *